(12) United States Patent
Freiman et al.

(10) Patent No.: US 11,039,804 B2
(45) Date of Patent: Jun. 22, 2021

(54) APPARATUS AND METHOD FOR DETERMINING A FRACTIONAL FLOW RESERVE

(71) Applicant: KONINKLIJKE PHILIPS N.V., Eindhoven (NL)

(72) Inventors: Mordechay Pinchas Freiman, Zichron-Yaakov (IL); Liran Goshen, Pardes-Hanna (IL); Hannes Nickisch, Hamburg (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 190 days.

(21) Appl. No.: 16/331,562

(22) PCT Filed: Sep. 15, 2017

(86) PCT No.: PCT/EP2017/073243
§ 371 (c)(1),
(2) Date: Mar. 8, 2019

(87) PCT Pub. No.: WO2018/050806
PCT Pub. Date: Mar. 22, 2018

(65) Prior Publication Data
US 2019/0209115 A1     Jul. 11, 2019

(30) Foreign Application Priority Data
Sep. 16, 2016    (EP) ..................................... 16189223

(51) Int. Cl.
*A61B 6/00*      (2006.01)
*A61B 5/02*      (2006.01)
(Continued)

(52) U.S. Cl.
CPC .............. *A61B 6/504* (2013.01); *A61B 5/026* (2013.01); *A61B 5/02007* (2013.01);
(Continued)

(58) Field of Classification Search
CPC ......... G06T 7/0012; G06T 2207/30048; G06T 2207/30104; G06T 7/20; G06T 7/60;
(Continued)

(56) References Cited

U.S. PATENT DOCUMENTS 8,157,742 B2 * 4/2012 Taylor .................... G16H 50/50
                                                                600/504
8,200,466 B2   6/2012 Spilker
(Continued)

FOREIGN PATENT DOCUMENTS

DE        102008014792      6/2009
EP            2825091       1/2015
(Continued)

OTHER PUBLICATIONS

Finegold, et al.: "Mortality from ischaemic heart disease by country, region, and age: Statistics from World Health Organisation and United Nations", Int J Cardiol 168(2), 934-945 (2013).
(Continued)

*Primary Examiner* — Dung Hong
(74) *Attorney, Agent, or Firm* — Larry Liberchuk

(57) ABSTRACT

The present invention relates to an apparatus (26) and a method for determining a fractional flow reserve. For this purpose, a new personalized hyperemic boundary condition model is provided. The personalized hyperemic boundary condition model is used to condition a parametric model for a simulation of a blood flow in a coronary tree (34) of a human subject. As a basis for the personalized hyperemic boundary condition model, a predefined hyperemic boundary condition model is used, which represents empirical derived hyperemic boundary condition parameters. However, these empirical hyperemic boundary condition parameters are not specific for a human subject under examination. In order to achieve a specification of the respective pre-
(Continued)

defined hyperemic boundary condition model, specific human subject features are derived from a volumetric image of the coronary tree of the human subject. These features are used to adjust the predefined hyperemic boundary condition model resulting in a personalized hyperemic boundary condition model. As an effect, a flow simulation using the parametric model conditioned by the personalized hyperemic boundary condition model. As an effect, a flow simulation using the parametric model conditioned by the personalized hyperemic boundary condition model improves the performance of flow simulation in order to determine an enhanced fractional flow reserve.

11 Claims, 3 Drawing Sheets

(51) Int. Cl.
| | | |
|---|---|---|
| G16H 50/50 | (2018.01) | |
| G16H 30/40 | (2018.01) | |
| A61B 5/026 | (2006.01) | |
| G06T 7/00 | (2017.01) | |

(52) U.S. Cl.
CPC ............ *A61B 6/507* (2013.01); *G16H 30/40* (2018.01); *G16H 50/50* (2018.01); *A61B 5/0263* (2013.01); *A61B 6/481* (2013.01); *A61B 2576/023* (2013.01); *G06T 7/0012* (2013.01)

(58) Field of Classification Search
CPC ........ G06T 17/005; G06T 2207/30101; G16H 50/50; A61B 5/02007; A61B 5/021; A61B 5/026
See application file for complete search history.

(56) References Cited

U.S. PATENT DOCUMENTS

| | | | |
|---|---|---|---|
| 8,249,815 | B2 | 8/2012 | Taylor |
| 9,119,540 | B2 | 9/2015 | Sharma |
| 9,268,902 | B2 | 2/2016 | Taylor |
| 2010/0125197 | A1 | 5/2010 | Fishel |
| 2010/0130878 | A1 | 5/2010 | Lasso |
| 2010/0241404 | A1 | 9/2010 | Taylor |
| 2011/0096892 | A1* | 4/2011 | Forthmann .......... A61B 6/4241 378/5 |
| 2011/0211742 | A1 | 9/2011 | Bredno |
| 2011/0307231 | A1 | 12/2011 | Kirchner |
| 2012/0022843 | A1 | 1/2012 | Ionasec |
| 2012/0041318 | A1* | 2/2012 | Taylor .................. A61B 5/0044 600/504 |
| 2012/0041319 | A1 | 2/2012 | Taylor |
| 2012/0041320 | A1 | 2/2012 | Taylor |
| 2012/0041321 | A1 | 2/2012 | Taylor |
| 2012/0041322 | A1 | 2/2012 | Taylor |
| 2012/0041323 | A1 | 2/2012 | Taylor |
| 2012/0041324 | A1 | 2/2012 | Taylor |
| 2012/0041325 | A1 | 2/2012 | Taylor |
| 2012/0041739 | A1 | 2/2012 | Taylor |
| 2012/0053919 | A1 | 3/2012 | Taylor |
| 2012/0059246 | A1 | 3/2012 | Taylor |
| 2012/0072190 | A1* | 3/2012 | Sharma ................. G06T 7/0016 703/2 |
| 2012/0121151 | A1 | 5/2012 | Bernhardt |
| 2012/0243761 | A1 | 9/2012 | Senzig |
| 2012/0296199 | A1 | 11/2012 | Kim |
| 2013/0246034 | A1* | 9/2013 | Sharma .................. A61B 6/503 703/11 |
| 2014/0058715 | A1 | 2/2014 | Sharma |
| 2014/0114618 | A1 | 4/2014 | Fonte |
| 2015/0038860 | A1 | 2/2015 | Fonte |
| 2015/0051888 | A1 | 2/2015 | Itu |
| 2015/0065864 | A1* | 3/2015 | Sharma ................ A61B 5/0263 600/416 |
| 2015/0245775 | A1 | 9/2015 | Fonte |
| 2015/0348260 | A1 | 12/2015 | Sharma |
| 2016/0066800 | A1 | 3/2016 | Sharma |
| 2016/0106321 | A1 | 4/2016 | Sharma |
| 2016/0133015 | A1 | 5/2016 | Taylor |
| 2016/0166209 | A1* | 6/2016 | Itu ...................... A61B 5/02028 600/408 |
| 2017/0032097 | A1* | 2/2017 | Itu .......................... G16H 50/50 |
| 2017/0046834 | A1* | 2/2017 | Itu ........................ A61B 5/0263 |
| 2017/0068797 | A1* | 3/2017 | Sharma .................. A61B 6/507 |

FOREIGN PATENT DOCUMENTS

| | | |
|---|---|---|
| WO | 00/72037 | 11/2000 |
| WO | 2004025572 | 3/2004 |
| WO | 200661814 | 6/2006 |
| WO | 200661815 | 6/2006 |
| WO | 201022762 | 3/2010 |
| WO | 2015017571 | 2/2015 |
| WO | 2015/171376 | 11/2015 |
| WO | 2016001017 | 1/2016 |
| WO | 2017076620 | 5/2017 |

OTHER PUBLICATIONS

Arbab-Zadeh, et al.: "Quantification of coronary arterial stenoses by multidetector CT angiography in comparison with conventional angiography methods, caveats, and implications", JACC Cardiovasc Imaging 4(2), 191-202 (2011).

Meijboom, et al.: "Comprehensive assessment of coronary artery stenoses: computed tomography coronary angiography versus conventional coronary angiography and correlation with fractional flow reserve in patients with stable angina", Journal of the American College of Cardiology, vol. 52, Issue 8, Aug. 19, 2008, pp. 636-643.

Nørgaard, et al.: "Diagnostic performance of noninvasive fractional flow reserve derived from coronary computed tomography angiography in suspected coronary artery disease: the NXT trial (Analysis of Coronary Blood Flow Using CT Angiography: Next Steps", Journal of the American College of Cardiology, vol. 63, Issue 12, Apr. 1, 2014, pp. 1145-1155.

Coenen, et al.: "Fractional Flow Reserve Computed from Noninvasive CT Angiography Data: Diagnostic Performance of an On-Site Clinician-operated Computational Fluid Dynamics Algorithm", Radiology 274(3), 674-683 (2015).

Vignon-Clementel, et al.: "Outflow boundary conditions for 3D simulations of non-periodic blood flow and pressure fields in deformable arteries", Computer methods in biomechanics and biomedical engineering 13(5), 625-640 (2010).

Sharma, et al.: "A framework for personalization of coronary flow computations during rest and hyperemia", In Engineering in Medicine and Biology Society (EMBC), 2012 Annual International Conference of the IEEE (pp. 3665-6668). IEEE (2012).

Taylor, et al.: "Computational fluid dynamics applied to cardiac computed tomography for noninvasive quantification of fractional flow reserve: scientific basis", Journal of the American College of Cardiology, 61(22), pp. 2233-2241 (2013).

Nickisch, et al.: "Learning Patient-Specific Lumped Models for Interactive Coronary Blood Flow Simulations", MICCAI 2015: Medical Image Computing and Computer-Assisted Intervention— MICCAI 2015 pp. 433-441.

* cited by examiner

APPARATUS AND METHOD FOR DETERMINING A FRACTIONAL FLOW RESERVE

CROSS REFERENCE TO RELATED APPLICATIONS

This application is the U.S. National Phase application under 35 U.S.C. § 371 of International Application No. PCT/EP2017/073243 filed Sep. 15, 2017, published as WO 2018/050806 on Mar. 22, 2018, which claims the benefit of European Patent Application Number 16189223.7 on Sep. 16, 2016. These applications are hereby incorporated by reference herein.

FIELD OF THE INVENTION

The present invention relates to an apparatus for determining a fractional flow reserve and to a method for determining a fractional flow reserve.

BACKGROUND OF THE INVENTION

Cardiovascular diseases are a leading cause of death in the industrialized world. The predominant form of cardiovascular disease results from the chronic build-up of a fatty material in the inner tissue layer of the arteries supplying the heart, brain, kidneys and lower extremities. Progressive coronary artery disease restricts blood flow to the heart. Due to the lack of accurate information provided by current non-invasive tests, many patients require invasive catheter procedures to assess a coronary blood flow. Accordingly, there is a need for a non-invasive approach to quantify blood flow in the human coronary arteries to assess the functional significance of a possible coronary artery disease. A reliable assessment of artery capacity would therefore be important for treatment planning to address patient needs. Recent studies have demonstrated that hemodynamic characteristics, such as fractional flow reserve (FFR), are important indicators to determine the optimal treatment for a patient with arterial disease. Conventional assessments of the fractional flow reserve use invasive catheterization to directly measure blood flow characteristics, such as pressure and flow velocities. However, these invasive measurement techniques present a risk to the patient and may result in significant costs to the health care system.

Fractional flow reserve is an index of the functional severity of a coronary stenosis that is calculated from pressure measurements preferable made during coronary arteriography—and is defined as the distal blood pressure (behind a stenosis) relative to the proximal pressure (close to the ostium) under hyperemic conditions (i.e. the ratio between the pressure after a lesion and the normal pressure). In other words, the fractional flow reserve expresses the maximum flow down a coronary vessel, in particular in the presence of a stenosis compared to the maximal flow in the hypothetical absence of the stenosis. A fractional flow reserve is a value in an absolute number between 0 and 1, wherein the fractional flow reserve of 0.5 indicates that a given stenosis causes a 50% drop in blood pressure, which preferably facilitates a diagnosis of the extent of a stenosis.

Computed tomography arterial angiography is a computed tomography technique used to visualize artery vessels. For this purpose, beams of X-rays are passed from a radiation source through an area of interest in the patient's body to obtain a projection image. Preferably, the X-rays are passed through the patient's body from several different angles to obtain a respective projection image, which are then assembled by a processing unit into a three-dimensional image representing the area of interest of the patient's body. Thus, computed tomography coronary angiography is a non-invasive technique for the evaluation of coronary artery disease. The high negative predictive value in coronary artery disease detection positions the computed tomographic coronary angiography as a non-invasive technique to rule out coronary artery disease in symptomatic patients with low to intermediate pre-test probability of disease. However, computed tomography coronary angiography is limited in assessing hemodynamic significance of coronary lesions. Assessing hemodynamic significance from computed tomography coronary angiography requires accurate segmentation of the coronaries to generate a three-dimensional model for flow simulations and a boundary condition model that models the interface with non-image vasculature. While automatic or semi-automatic tools are available for generating a three-dimensional model of the coronary tree from the computed tomography coronary angiography image data, accurate modelling of the boundary condition remains a significant challenge.

From US 2013/0246034 A1 it is known to acquire a FFR with a framework that includes an image acquisition stage, an anatomical modeling stage, a blood flow simulation stage, and a FFR computation phase. In the image acquisition stage, non-invasive data from the patient are acquired. The blood flow simulation stage uses that data to build a patient specific model of the coronary arteries. Then the blood flow in the coronary arteries is simulated. Hyperemic boundary conditions are modelled based on that simulation.

It is known how to couple analytic models, such as resistance models, impedance models or Windkessel models into the boundaries of a truncated computational domain. However, these models use constant parameters based on empirical measurements. In practice, there is a large variability between measurements of different human individuals. Moreover, the capillaries' resistance may be auto-regulated to account for presence of stenosis in the apparent coronary. Collateral flow is an auto-regulated mechanism used by the human body to prevent ischemia in the case of coronary stenosis by creating new arterials that support collateral blood flow to the potential ischemic region. Even in the absence of obstructive coronary artery disease or in entirely normal hearts, there may be collateral flow to a briefly occluded coronary artery sufficient to prevent ECG signs of myocardial ischemia in 20% to 25% of the population. However, due to the small diameter of the collateral arterials, computed tomography coronary angiography may not directly depict the presence of collateral arterials that support collateral blood flow. As a result, currently used boundary conditions models do not account for the presence of collateral flow. Unfortunately, this and/or other human subject's specific properties of a coronary tree may cause inaccurate estimation of the fractional flow reserve.

SUMMARY OF THE INVENTION

In view of the previous explanations, there may be a need to better account for patient's differences in the coronary blood flow, when using a model for simulating a blood flow in the coronary tree with boundary conditions.

The object of the present invention is solved by the subject-matter of the independent claims, wherein further embodiments are incorporated in the dependent claims. It should be noted that the following described aspects of the invention apply also for the method, the computer program element and the computer-readable medium, at least in an analogous manner.

According to a first aspect of the present invention, an apparatus for determining a fractional flow reserve is provided. The apparatus comprises an input interface, a processing unit and a storage means. The input interface is configured to obtain volumetric image data representing a coronary tree of a human subject. The storage means is configured to provide a parametric model for simulating a blood flow in a coronary tree. The storage means is configured to provide a hyperemic boundary condition model representing at least one predefined hyperemic boundary condition parameter for the parametric model. The processing unit is configured to extract at least one personalized feature from the volumetric image data. The processing unit is configured to adapt the hyperemic boundary condition model based on the at least one personalized feature resulting in a personalized hyperemic boundary condition model. Further, the processing unit is configured to determine a fractional flow reserve of a coronary vessel of the coronary tree of the human subject with the parametric model and the personalized hyperemic boundary condition model.

Preferably, the volumetric image data may be provided to the input interface of the apparatus from a reconstruction unit, which may be assigned to a computed tomography scanner. Accordingly, the volumetric image data preferably represents at least a section of a coronary tree of the human subject. The input interface may be connected to the processing unit, such that the volumetric image date can be provided to the processing unit. The storage means may be formed by a memory, in particular a data memory. Thus, the parametric model and the hyperemic boundary condition model may be stored by the storage means. The storage means may be connected to the processing unit, such that the parametric model and the hyperemic boundary condition model can be provided to the processing unit.

The parametric model is preferably configured for simulating a blood flow in a coronary vessel of the coronary tree of a human subject. The parametric model can be used by the processing unit to simulate the blood flow in the coronary tree, in particular in a blood vessel of the coronary tree, with hyperemic boundary condition parameters. Accordingly, the at least one hyperemic boundary condition parameter represents respective condition parameters for the parametric model, in order to simulate the blood flow in the coronary tree of the human subject in an hyperemic state. As this is a simulation, the hyperemic state of the human subject preferably relates to a hypothetical hyperemic state of the human subject. The hyperemic boundary condition parameters can be provided by the hyperemic boundary condition model. The hyperemic boundary condition parameters provided by the hyperemic boundary condition model are predefined. Thus, these parameters are predefined hyperemic boundary condition parameters. Preferably, these predefined hyperemic boundary condition parameters represent or are based on empirical hyperemic boundary condition parameters, which may be generated from prior analysis of a plurality of human subjects. Thus, the hyperemic boundary condition model as such is not personalized when being used with the parametric model. Thus, the hyperemic boundary conditions model as such may not account for the presence of the human subject's individual blood flow. Thus, an accurate blow flow simulation for the human subject's coronary tree would require personalized hyperemic boundary conditions for the parametric model.

In order to personalize the hyperemic boundary conditions for the parametric model, at least one personalized feature is extracted via the processing unit from the volumetric image data. The at least one personalized feature represents at least one property of the human subject and/or a property of the coronary tree of the human subject. Further preferred, the at least one personalized feature represents a property of a coronary vessel of the coronary tree of the human subject.

Further, the hyperemic boundary condition model is adapted based on the at least one personalized feature via the processing unit resulting in the personalized hyperemic boundary condition model. The personalized hyperemic boundary condition model preferably represents at least one personalized hyperemic boundary condition parameter for the parametric model. Thus, the adaptation may be performed, such that the personalized hyperemic boundary condition parameter indicates and/or reflects the personalized feature of the human subject. As a result, the personalized hyperemic boundary condition parameter may provide a condition for the parametric model in order to account for the human subject's individual blood flow characteristics in its coronary tree, which in turn provides more exact simulation results.

The fractional flow reserve of a coronary vessel of the coronary tree of the human subject is determined via the processing unit with the parametric model and the personalized hyperemic boundary condition model. The determination of the fractional flow reserve may also refer to an estimation of the fractional blood flow reserve. The parametric model is conditioned by the at least one hyperemic boundary condition parameter of the personalized hyperemic boundary condition model. In other word, the fractional flow reserve of the coronary vessel may be determined by the parametric model under condition of the at least one, in particular adapted and/or personalized, hyperemic boundary condition parameter provided by the personalized hyperemic boundary condition model. As an effect, a vasculature, which has not been represented by the volumetric image data and/or which has not been imaged, may be represented by the personalized hyperemic boundary condition model. However, the volumetric image data may provide the basis for the extraction of a personalized feature of the human subject. This provides a basis for the adaptation of the hyperemic boundary condition model, in particular to adapt and/or adjust a predefined hyperemic boundary condition parameter thereof and/or to provide a further personalized hyperemic boundary condition parameter. Thus, the personalized feature may characterize the relationship between the non-image vasculature of the coronary tree of the human subject and a predefined hyperemic boundary condition parameter. Alternatively or additionally, the personalized feature may characterize the relationship between the non-image vasculature of the coronary tree of the human subject and a (further) personalized hyperemic boundary condition parameter. As a result, the personalized used hyperemic boundary conditions model accounts for the human subject's individual property of the coronary tree, which in turn result in a determination of the fractional flow reserve.

The adaptation of the hyperemic boundary condition model can be performed prior to the simulation as such. Thus, the processing unit of the apparatus may be configured to adapt the hyperemic boundary condition model prior to the simulation. As an effect, the parametric model and the personalized hyperemic boundary condition model may be provided without any pre-simulation of the blood flow in the coronary tree of the human subject. As a further result, the apparatus may be configured for a "one-phase" approach to determine the fractional flow reserve. Consequently, the apparatus provides an enhanced approach for performing a rapid, non-invasive, computationally inexpensive, enhanced determination of the fractional flow reserve of a coronary vessel of a coronary tree of a human subject.

According to an exemplary embodiment, the volumetric image data represents the coronary tree of the human subject in a rest state. As a result, risks and costs associated with the acquiring of the volumetric image data may be reduced. Further, the volumetric image data may be acquired independently and/or prior of an invasive treatment of the human subject.

According to a further exemplary embodiment, the processing unit is configured to determine the fractional flow reserve of the coronary vessel of the human subject in a hyperemic state. The hyperemic state of the human subject preferably relates to a hypothetical hyperemic state of the human subject. This results from the effect, that the fractional blood flow reserve is determined via a simulation. For this purpose, the processing unit is configured to simulate the blood flow of the coronary tree of the human subject in an (hypothetical) hyperemic state with the parametric model and the personalized hyperemic boundary condition model. As a result, an enhanced determination of the fractional flow reserve of the coronary vessel may be provided. As a further effect, a possible coronary lesion hyperdynamic significance may be estimated based on the determined fractional flow reserve. As an even further effect, invasive catheterization to directly measure blood flow characteristics of the coronary vessel of the human subject in a hyperemic state can be prevented.

According to a further exemplary embodiment, the volumetric image data is formed and/or based on cardiac computed tomography angiography image data. Further preferably, the volumetric image data may be determined based on computed tomography image data.

According to a further exemplary embodiment, the processing unit is configured to determine at least one personalized hyperemic boundary condition parameter based on the at least one personalized feature, wherein the processing unit is configured to adapt the hyperemic boundary condition model, such that the resulting personalized hyperemic boundary condition model comprises the at least one predefined hyperemic boundary condition parameter and the at least one personalized hyperemic boundary condition parameter. In comparison to the hyperemic boundary condition model, the personalized hyperemic boundary condition model comprises at least one further hyperemic boundary condition parameter, namely the at least one personalized hyperemic boundary condition parameter. Since the personalized feature may characterize a specific property of the coronary tree of the human subject under examination, in particular related to the coronary vessel of the coronary tree of the human subject, the at least one personalized hyperemic boundary condition, being determined based on said personalized feature, may therefore characterize a corresponding condition for the parametric model. As a result, an improved fractional flow reserve of the coronary vessel of the coronary tree of the human subject under examination can be determined.

According to a further exemplary embodiment, the processing unit is configured to determine the personalized hyperemic boundary condition model by adapting the at least one predefined hyperemic boundary condition parameter based on the at least one personalized feature. Thus, based on the at least one personalized feature, an adaptation or adjustment of the at least one predefined hyperemic boundary condition parameter may be performed, such that the adapted and/or adjusted at least one predefined hyperemic boundary condition parameter is characterized for the coronary tree of the human subject under examination. As a result, the previously, at least one predefined hyperemic boundary condition parameter, or at least one parameter thereof, is personalized based on the at least one personalized feature. Consequently, the personalized hyperemic boundary condition model is provided, which is specific for the coronary tree of the human subject. As an effect, the parametric model conditioned by the personalized hyperemic boundary condition model provides the basis for an enhanced simulation of blood flow in a coronary vessel of the coronary tree of the human subject, which in turn provides the basis for an improved determination of a fractional flow reserve of said coronary vessel.

According to a further preferred embodiment, the at least one personalized feature represents at least one anatomic feature of the coronary tree. Preferably, the at least one personalized feature represents at least one anatomic feature of the coronary vessel of the coronary tree. The coronary tree relates to the coronary tree of the human subject. The coronary tree of the human subject is represented by the volumetric image data. Thus, the corresponding volumetric image allows to extract an anatomical feature of the coronary tree of the human subject. This extraction is performed by the processing unit. Generally, a volumetric image of the coronary tree of the human subject provides several anatomical features. For the at least one personalized feature, at least one of these anatomical features is extracted in order to form and/or extract the at least one personalized feature. Each anatomical feature is specific for the human subject under examination and therefore is specific to the coronary tree of the human subject. Thus, an anatomical feature of the coronary tree of the human subject provides the basis for determining a personalized hyperemic boundary condition parameter and/or for the adaptation of a predefined hyperemic boundary condition parameter. Therefore, each of said parameters may characterize a specific coronary tree hyperemic boundary condition parameter. As an effect, an improved determination of the fractional flow reserve is available.

According to a further preferred embodiment, the at least one anatomical feature represents a cross-section of a segment of the coronary tree. Preferably, the segment refers to the coronary vessel of the coronary tree. A cross-section of a segment of a coronary tree of the human subject under examination may represent or indicate a flow resistance at said segment of the coronary tree. As a result, a flow resistance may be calculated from the cross-section of the segment of the coronary tree for the respective segment. As an effect, the cross-section of the segment of the coronary tree provides a specific or personalized feature of the coronary tree of the human subject under examination. Thus, the cross-section of the segment of the coronary tree provides a basis for the adaptation of the predefined condition model and/or a basis for determining a (further) personalized hyperemic boundary condition parameter. As a result, a human subject specific, namely personalized, hyperemic boundary condition model can be provided for conditioning the parametric model in order to simulate a blood flow in the coronary tree, in particular in the coronary vessel of the coronary tree of the human subject. As an effect, an improved determination of a fractional flow reserve is available.

According to a further preferred embodiment, the at least one personalized feature represents at least one morphological feature of the coronary tree. Preferably, the at least one personalized feature represents at least one morphological feature of the coronary vessel of the coronary tree. A morphological feature of the coronary tree may relate to and/or represent a feature of a tissue forming a surrounding surface of the coronary vessel of the coronary tree. Preferably, the tissue is assumed to be assigned to the coronary tree. Typically, a coronary vessel of a coronary tree provides a smooth, elastic inside aligning. However, a coronary vessel of a coronary tree may become hardened, stiffened, swollen and/or subject to deposits. As a result, the surrounding tissue may be subject to a corresponding change, which may be represented and/or indicated by the morphological feature. Therefore, the at least one morphological feature of the coronary tree provides the basis for the adaptation of the hyperemic boundary condition model resulting in the personalized hyperemic boundary condition model. With respect to the effects and/or advantages of such a personalized hyperemic boundary condition model, reference is made in an analogous manner to the explanation provided above. In particular, an improved determination of the fractional flow reserve is possible.

According to a further preferred embodiment, the at least one morphological feature represents plaque in the coronary tree, in particular in the coronary vessel thereof. Thus, the morphological feature may represent plaque deposits in the tissue forming the coronary tree, and in particular a coronary vessel thereof. Plaque may be formed by calcium deposits and/or fatty deposits in the tissue forming the coronary tree and/or its at least one coronary vessel. Plaque may result in a hardened, stiffened and/or swollen coronary vessel, which further results in a reduced cross-section of said coronary vessel and/or in an increased flow resistance. Thus, a morphological feature representing plaque in the coronary tree provides a good basis to adapt and/or adjust the predefined hyperemic boundary condition model in order to receive the enhanced personalized hyperemic boundary condition model. With respect to the effects and/or results of said personalized hyperemic boundary condition model, reference is made in an analogous manner to the previous explanations provided above. In particular, an improved determination of the fractional flow reserve is possible.

According to a further predefined embodiment, the at least one personalized feature represents at least one spectral feature of the coronary tree, in particular in the coronary vessel thereof. The spectral feature of the coronary tree may represent and/or indicate a concentration of different materials of the tissue forming the coronary tree. As a result, a personalized feature representing the spectral feature of the coronary tree provides a good basis for determining a personalized hyperemic boundary condition parameter and/or to adapt the at least one predefined hyperemic boundary condition parameter. With respect to the advantage and/or the effects of a personalized hyperemic boundary condition model, reference is made in an analogous manner to the previous provided explanations. In particular, an improved determination of the fractional flow reserve is possible.

According to a preferred embodiment, the at least one spectral feature represents a concentration of plaque material in the coronary tree, in particular in the coronary vessel thereof. The spectral feature of the coronary tree may represent and/or indicate a plaque concentration of at least on plaque material in the tissue forming the coronary tree. With respect to the advantages and/or effects of this embodiment, reference is made in an analogous manner to the previous explanations.

According to a second aspect of the present invention, a method for determining a fractional flow reserve is provided. The method comprises the following steps:
a) Obtaining volumetric image data representing a coronary tree of a human subject;
b) Providing a parametric model for simulating a blood flow in a coronary tree;
c) Providing a hyperemic boundary condition model representing at least one predefined hyperemic boundary condition parameter for the parametric model;
d) Extracting at least one personalized feature from the volumetric image data;
e) Adapting the hyperemic boundary condition model based on the at least one personalized feature resulting in a personalized hyperemic boundary condition model; and
f) Determining a fractional flow reserve of a coronary vessel of the coronary tree of the human subject with the parametric model and the personalized hyperemic boundary condition model.

It is understood that, without repeating here all the explanations, examples, features and/or advantages provided with respect to the apparatus, the method of the invention is intended to be configured to carry out the method steps for which the apparatus is configured to. Thus, all the above provided examples, explanations, features and/or advantages, although provided previously with reference to the apparatus, are also to be intended as being provided in an analogous manner for the method of the invention.

According to a third aspect of the present invention, a computer program element for controlling an apparatus of the invention is provided, which, when being executed by a processing unit, is adapted to carry out the method described above.

According to a fourth aspect of the present invention, a computer-readable medium having stored thereon the program element is provided, which, when being executed by a processing unit, is adapted to carry out the method described above.

According to an aspect of the present invention, a new personalized hyperemic boundary condition model is provided. The personalized hyperemic boundary condition model is used to condition a parametric model for a simulation of a blood flow in a coronary tree of a human subject. As a basis for the personalized hyperemic boundary condition model, a predefined hyperemic boundary condition model is used, which represents empirical derived hyperemic boundary condition parameters. However, these empirical hyperemic boundary condition parameters are not specific for a human subject under examination. In order to achieve a specification of the respective predefined hyperemic boundary condition model, specific human subject features are derived from a volumetric image of the coronary tree of the human subject. These features are used to adjust the predefined hyperemic boundary condition model resulting in a personalized hyperemic boundary condition model. As a result, a flow simulation using the parametric model conditioned by the personalized hyperemic boundary condition model improves the performance of flow simulation in order to determine an enhanced fractional flow reserve. The accuracy of such simulation highly depends upon accurate geometrical modelling of the coronary tree and the hyperemic boundary condition that models the interface with non-image vasculature. The personalized feature extracted from the volumetric image of the coronary tree addresses the potential biases in flow of the coronary tree, such that the personalized hyperemic boundary condition model provides an enhanced and an even more specific set of parameters representing specific characteristics of the coronary tree of the human subject under examination. The extracted personalized features may relate to anatomical features, morphological features or spectral features of the coronary tree. The personalized hyperemic boundary condition model as well as the parametric model can be provided in beforehand of a simulation. Moreover, the personalized feature of the coronary tree of the human subject under examination may be acquired during a rest state of the human subject. Due to the specification of the hyperemic boundary condition by the personalized hyperemic boundary condition model to the specific human subject, an enhanced blood flow simulation may be performed, which in turn results in an enhanced determination of fractional flow reserve of the coronary tree, and in particular of a coronary vessel of the coronary tree of the human subject under examination.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

In the following, the invention is exemplarily described as being used in the context of the apparatus for determining a fractional flow reserve. But the invention can also be used in the context of the method for determining a fractional flow reserve. Thus, all the following examples and/or explanations may also be intended as being implemented by the method of the invention.

Figure 1:
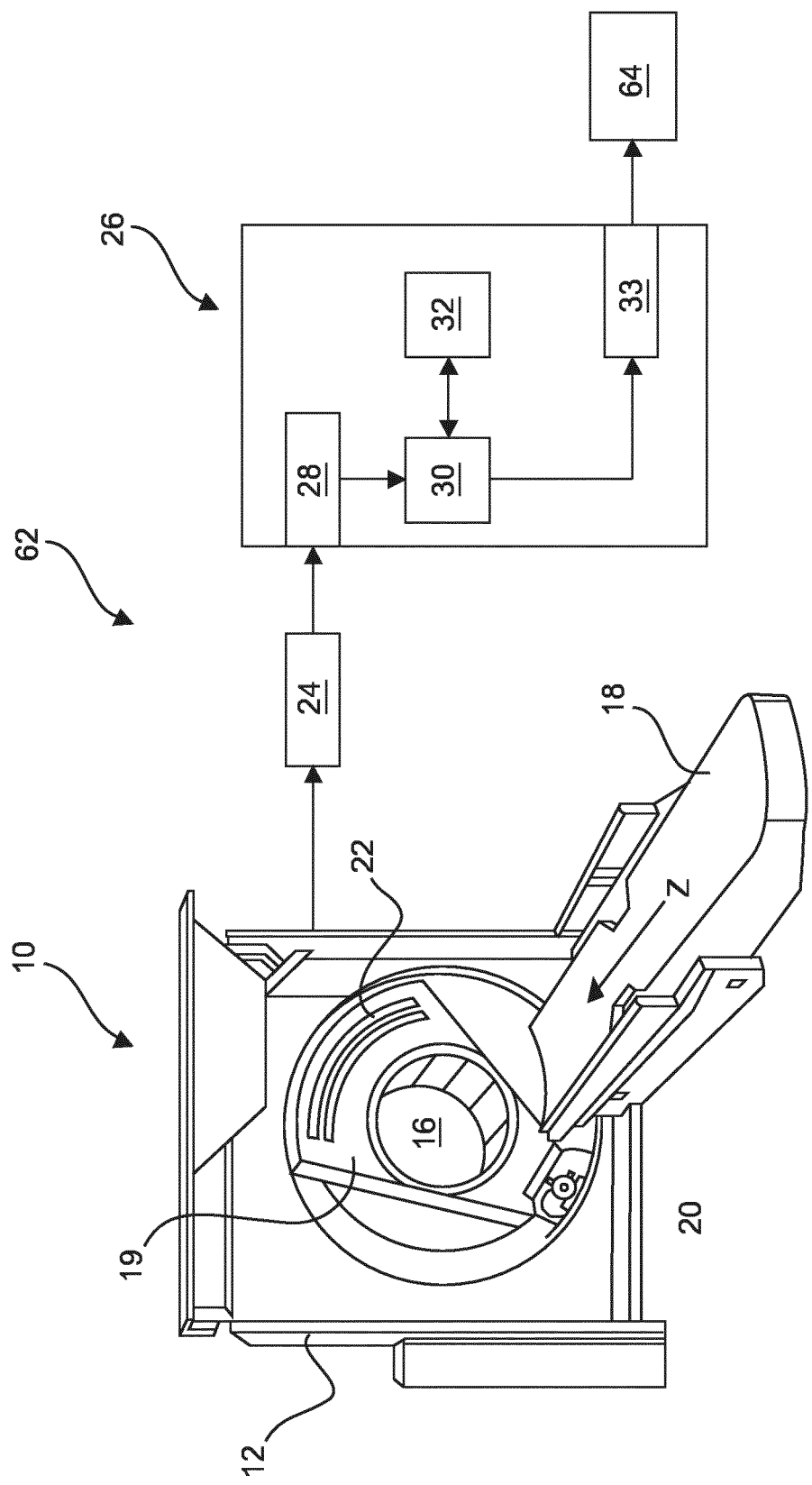
FIG. 1 schematically illustrates a system for acquiring volumetric image data of a coronary tree of a human subject and an exemplary embodiment of the apparatus for determining a fractional flow reserve.

FIG. 1 schematically illustrates on the left-hand side an imaging system 10. Preferably, the imaging system 10 is a computer tomography scanner. Further preferred, the imaging system 10 is configured at least for coronary computed tomography angiography scans and/or procedures. The imaging system 10 additionally or alternatively may include an X-ray scanner, a magnetic resonance imaging scanner and/or another scanner configured for coronary computed tomography angiography scans.

The imaging system 10 may comprise a stationary gantry 12. The stationary gantry 12 rotatably supports a rotating gantry 14. The rotating gantry 14 is configured to rotate around an examination region 16. The imaging system 10 further comprises a subject support 18. The subject support 18 is configured to support a human subject into the examination region 16. The imaging system 10 further comprises a radiation source 20. The radiation source, such as an X-ray tube, is supported by the rotating gantry 14, rotates with the rotating gantry 14, and is configured to emit radiation that transverses the examination region 16.

The imaging system 10 further comprises a radiation sensitive detector array 22. The radiation sensitive detector array 22 subtends an angular arc opposite the radiation source 20 across the examination region 16, and is configured to detect radiation traversing the examination region 16 and to generate a signal (projection data) indicative thereof. The imaging system 10 further comprises a reconstruction unit 24. The reconstruction unit 24 is configured to generate, based on the signal of the radiation sensitive detector array 22, a volumetric image data representing a scanned portion of the human subject located in the examination region 16. Thus, the reconstruction unit 24 is configured to provide volumetric image data representing a coronary tree 34 of a human subject. For this purpose, the human subject is administrated (e.g., intravenously etc.) a radial-opaque contrast agent. Thus, the resulting volumetric image data is the coronary computed tomography angiography image data that visualizes and/or represents the blood vessels of the coronary tree 34 of the human subject, in particular blood vessels such as arteries, veins, etc. of the coronary tree 34.

Figure 2:
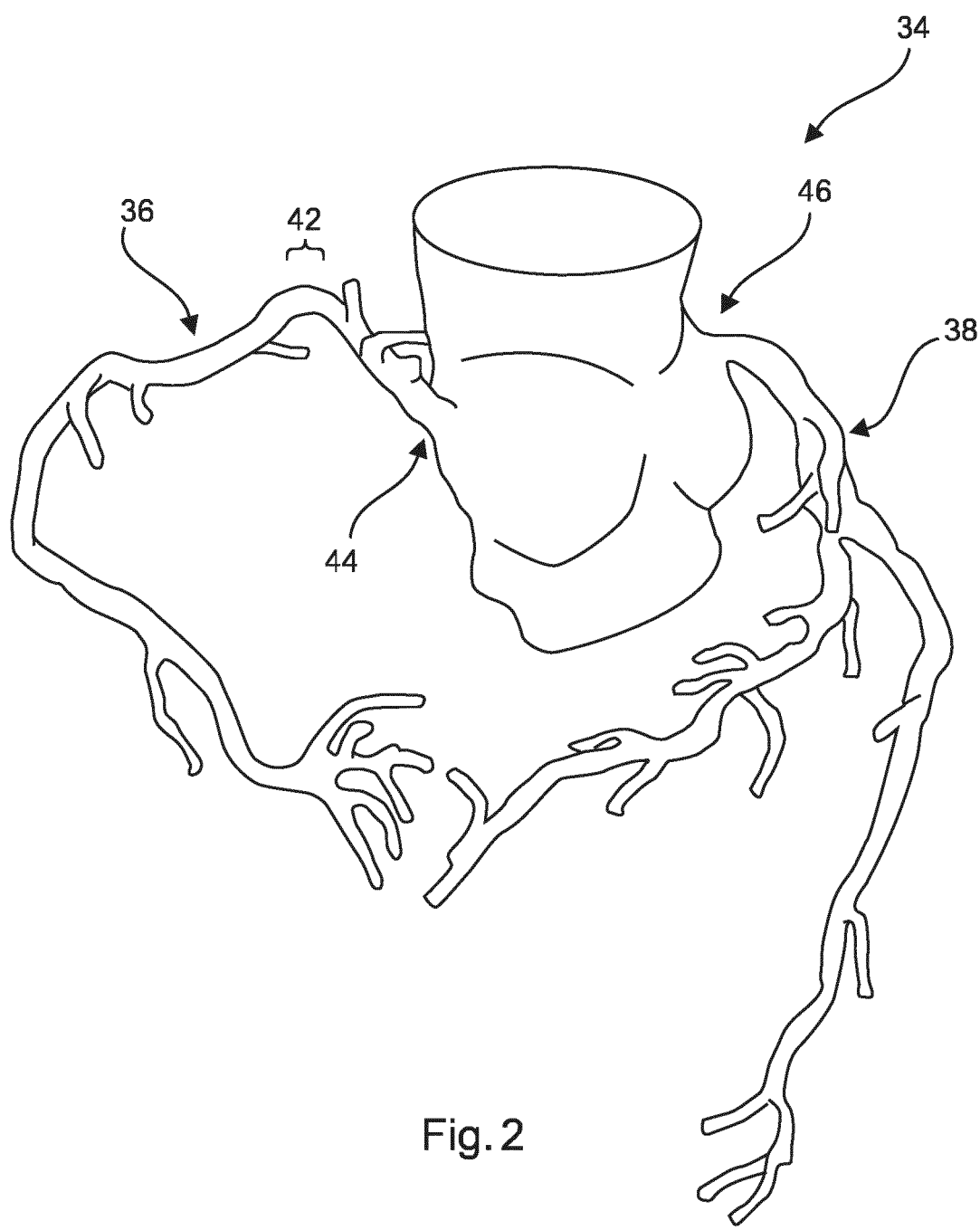
FIG. 2 schematically illustrates an example of a coronary tree.

FIG. 1 schematically illustrates on the right-hand side an apparatus 26 for determining a fractional flow reserve. The apparatus 26 comprises an input interface 28, a processing unit 30 and a storage means 32. The input interface 28 is configured to obtain volumetric image data representing a coronary tree 34 of a human subject. For this purpose, the volumetric image data may be transmitted from the reconstruction unit 24 to the input interface 28. An example of a coronary tree 34 of a human subject is exemplarily illustrated in FIG. 2. The coronary tree 34 comprises the right coronary artery 36 and the left coronary artery 38. Each of the coronary arteries 36, 38 may form a coronary vessel of the coronary tree 34. Further, if the input interface 28 obtains volumetric image data, this volumetric image data is human subject specific and represents therefore the specific coronary tree 34 of the human subject. As a result, the volumetric image data may represent personal features of the coronary tree 34, in particular of at least one coronary vessel thereof.

The storage means 32 of the apparatus 26 is configured to provide a parametric model for simulating a blood flow in a coronary tree of a human subject. The storage means 32 is preferably a data memory. The storage means 32 is preferably connected to the processing unit 30, in order to exchange data between the storage means 32 and the processing unit 30.

The parametric model provided by the storage means 32 is a generic model for simulating blood flow of a coronary tree of any human subject. Thus, the parametric model is not specific for the human subject under examination. Further, in order to condition the parametric model, the storage means 32 is configured to provide a hyperemic boundary condition model. The hyperemic boundary condition model represents at least one predefined hyperemic boundary condition parameter for the parametric model. However, the at least one predefined hyperemic boundary condition parameter is usually determined based on empirical data received from a plurality of representative human subjects. Thus, the predefined hyperemic boundary condition parameter is also not specific for the human subject under examination. As a result, neither the parametric model nor the predefined hyperemic boundary condition model account for specific properties of a coronary tree 34 of the individual human subject under examination.

In order to enable an accurate simulation of a blood flow in the coronary tree of a specific human subject, an enhanced hyperemic boundary condition model needs to be provided, which addresses the individual properties of the coronary tree of the specific human subject. For this purpose, the processing unit 30 is configured to extract at least one personalized feature from the volumetric image data. For instance, a personalized feature extracted from the volumetric image data representing the coronary tree of the specific human subject under examination may be a cross-sectional area of a coronary vessel inlet 44, 46 of the coronary tree 34 of the human subject under examination. The cross-section area provides a basis and/or an indication for the flow resistance in the respective coronary vessel 36, 38, which would have an impact on the blood flow simulation in the coronary tree 34. Thus, a personalized feature extracted from the volumetric image data can be taken as a basis for the adaptation of hyperemic boundary conditions for the parametric model, which in turn would be configured for the accurate simulation of blood flow in the coronary tree.

Therefore, the processing unit 30 is configured to adapt the hyperemic boundary condition model based on the at least one personalized feature resulting in a personalized hyperemic boundary condition model. In contrast to the hyperemic boundary condition model provided by the storage means 32, the personalized condition model provides at least one hyperemic boundary condition parameter, which is specific for the human subject under examination. The remaining condition parameters may correspond to the respective predefined condition parameters of the hyperemic boundary condition model provided by the storage means 32. As a result, the personalized hyperemic boundary condition model allows to condition the parametric model, such that an individualized blood flow simulation is enabled.

The apparatus 26 may further comprise an output interface 33. The output interface 33 may be configured to provide the determined fractional flow reserve.

Furthermore, according to a further aspect of the present invention, a system 62 may be provided comprising the imaging system 10 and the apparatus 26. Moreover, the system 66 may comprise a display 64. The display 64 may be connected to the output interface 33 of the apparatus 26, such that the determined fractional flow reserve can be provided to the display 62. The display 64 may be configured to illustrate the fractional flow reserve.

The models and the data for simulating the blood flow in the coronary tree 34 of the human subject under examination may be provided well before an actual treatment of the human subject. Moreover, for simulating the blood flow in the coronary tree 34 with enhanced accuracy, there is no need for a pre-simulation of the blood flow. Instead, the processing unit 30 is configured to determine a fractional flow reserve of a coronary vessel of the coronary tree 34 of the human subject under examination with the parametric model and the personalized hyperemic boundary condition model. Thus, the apparatus 26 is configured for a "one-phase" approach to determine the fractional flow reserve. This reduces the processing power needed for determining the fractional flow reserve.

Furthermore, the volumetric image data may relate to and/or represent the coronary tree 34 of the human subject in a rest state. Thus, the acquisition of the image data may be performed and/or the projection data—on which the image data may be based on—may be acquired at a rest state of the human subject. As an effect, the impact of the human subject can be reduced.

Due to the adjusted and/or adapted at least one hyperemic boundary condition parameter provided by the personalized hyperemic boundary condition model, the processing unit is configured to determine the fractional flow reserve of the coronary vessel of the coronary tree 34 of the human subject in a hyperemic state. However, the human subject under examination is not actually in the hyperemic state. But the personalized hyperemic boundary condition model allows a respective conditioning of the parametric model for simulating a blood flow in the coronary tree 34 of the human subject under examination. Thus, the blood flow can be simulated for a hyperemic state of the human subject under examination, which in turn allows to determine the fractional flow reserve of the coronary vessel of the coronary tree. As a result, the human subject has not to be brought into the actual hyperemic state in order to determine the fractional flow reserve. Instead, this can be simulated by means of the apparatus 26. As a further effect, coronary lesion hyperdynamic significance may be estimated based on the determined fractional flow reserve. A possible treatment of the human subject may be planned based on the coronary lesion hyperdynamic significance and/or based on the fractional flow reserve.

Figure 3:
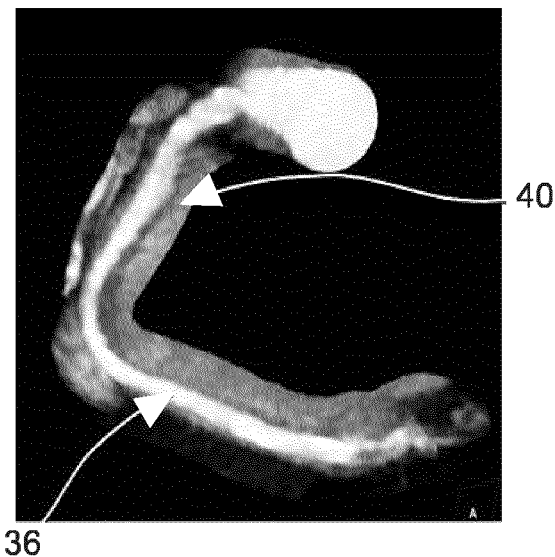
FIG. 3 schematically illustrates an example of a section of a coronary tree.

FIG. 3 schematically illustrates the right coronary artery 36 of the coronary tree 34 and a surrounding tissue region 40. The right coronary artery 36 may form a coronary vessel of the coronary tree 34. The surrounding tissue 40 may be subject to plaque deposits, in particular to calcium deposits or fatty deposits. As a result, the cross-section of the right coronary artery 36 may vary in its diameter and/or value, in particular resulting form said plaque. Plaque deposits in the surrounding tissue 40 may cause a hardening and/or stiffening and/or even a swallowing of the surrounding tissue 40. As a result, a blood flow resistance in such a region may be increased and thus, have in turn an impact on the fractional flow reserve.

In order to provide an accurate simulation of the blood flow in the coronary tree 34, and in particular of the right coronary artery 36, such human subject specific properties have to be taken into account for the simulation. For this purpose, the at least one personalized feature extracted from the volumetric image data representing the coronary tree 34 of the human subject represents at least one anatomical feature of the coronary tree 34, and in particular of the right coronary artery 36. For example, an anatomical feature of the coronary tree 34 may relate to the number of branches of the coronary tree 34, a cross-sectional area of the coronary tree 34 and/or other functional features of the coronary tree 34. In particular, at least one anatomical feature represents a cross-section of a segment 42 of the coronary tree 34. According to a further example, at least one anatomical feature represents a cross-section at an inlet 44 of the right coronary tree 36 and/or at an inlet 46 at the left coronary artery 38. According to an even further example, at least one anatomical feature represents a mean cross-section of the right coronary tree 36. The term "cross-section" may relate to a respective, in particular mean, cross section area, to a respective, in particular mean, cross section diameter or to a respective, in particular mean, cross section radius. In an analogous manner, an anatomical feature may also represent a cross-section of the left coronary artery 38 or another vessel of the coronary tree 34.

According to an example, a volumetric image represented by the volumetric image data may provide a resolution, which allows represent the coronary tree 34, in particular its main arteries and its branches. However, it may lack in a representation of vascular and/or small arteries, which contribute to the blood flow of the coronary tree 34. In particular, said vascular and/or small arteries may allow a blood flow, if a main or parent artery is subject to a stenosis. In order to account for such coronary tree specific properties of the human subject under examination, which in turn affects the fractional flow reserve, an anatomical feature extracted from the volumetric image data may indicate such a blood flow. For instance, the number of branches and/or the length of the branches may indicate a human subject's specific blood flow. In this case, a predefined hyperemic boundary condition parameter of the hyperemic boundary condition model may represent an inaccurate low blood flow resistance in the coronary tree 34, as it has been determined based on empirical data. In turn, a blood flow simulation based on a parametric model conditioned by the predefined hyperemic boundary condition parameters provided by the (impersonalized) hyperemic boundary condition model would result in an inaccurate fractional flow reserve result. In order to account for the lower blood flow resistance of the coronary tree 34 of the human subject under examination, the predefined hyperemic boundary condition parameter representing an inaccurate low blood flow resistance has to be adjusted and/or adapted by a further personalized hyperemic boundary condition parameter, to compensate the inaccuracy of the predefined hyperemic boundary condition parameter. A result thereof the personalized hyperemic boundary condition model is provided, which provides hyperemic boundary condition parameters, which are suitable to condition the parametric model, such that an accurate blood flow simulation of the coronary tree of the human subject is ensured. Such a simulation in particular simulates the blood flow in the exemplary explained coronary tree 34 with decreased blood flow resistance. Thus, the at least one anatomical feature as a personalized feature of the human subject may provide a good basis for adjusting and/or adapting a hyperemic boundary condition for the parametric model, in order to allow an accurate simulation of the blood flow through the coronary tree 34, which in turn provides an enhanced fractional flow reserve determination result.

According to an even further example, the processing unit 30 may be configured to perform the following steps in order to provide an anatomical feature of the coronary tree 34. Said steps are as follows:
i) determine an inlet cross-sectional area for each cross-section of the three main coronary tree branches,
ii) estimate the outlet cross-sectional area for each cross-section of the three main coronary tree branches,
iii) calculate a mean cross-sectional area for the previously determined inlet cross-sectional areas,
iv) calculate the mean cross-sectional area for the three outlet cross-sectional areas,
v) determine the mean cross-sectional area of the inlet cross-sections as the cross-sectional area to be an anatomical feature of the coronary tree 34, if the differences between the two mean cross-sectional areas is smaller than a predefined threshold. Otherwise, the mean cross-sectional area of the output cross-sectional areas is determined as the anatomical feature of the coronary tree 34.

According to a further preferred embodiment, at least one personalized feature represents at least one morphological feature of the coronary tree 34. As can be taken from FIG. 3, the surrounding tissue 40 surrounding the right coronary artery 36 of the coronary tree 34 may not be of a constant thickness. Instead, the surrounding tissue 40 may be subject to a plaque deposit, for instance a fatty deposit and/or a calcium deposit. The plaque deposit may in turn result in a plaque burden for the blood flow in the right coronary artery 36. The morphological feature of the coronary tree 34 extracted from the volumetric image data, and in particular of the right coronary artery 36, may therefore indicate or represent the amount of plaque in the surrounding tissue 40. Thus, a morphological feature of the coronary tree 34 may provide a value for the plaque deposit, a number of plaque deposits, a length of a plaque deposit, a thickness of a plaque deposit and/or another value representing the plaque deposit.

Further, the surrounding tissue 40 may be subject to another lesion, thus to an abnormal damage or a change of the surrounding tissue 40 as such. The morphological feature extracted from the volumetric image data may represent an indicating value for such a lesion, for instance the length of such a lesion. In particular depending on the amount of plaque and/or to the extent of the lesion, the blood flow resistance through the coronary tree 34, and in particular through the right coronary artery 36, may be influenced, in particular increased. In this case, a predefined hyperemic boundary condition parameter of the hyperemic boundary condition model may represent an inaccurate low blood flow resistance, as it has been determined based on empirical data. In turn, a blood flow simulation based on a parametric model conditioned by the predefined hyperemic boundary condition parameters provided by the (impersonalized) hyperemic boundary condition model would result in an inaccurate fractional flow reserve result. In order to account for the higher blood flow resistance of the coronary tree 34 of the human subject under examination, the predefined hyperemic boundary condition parameter representing an inaccurate low blood flow resistance has to be adjusted and/or adapted by a further personalized hyperemic boundary condition parameter, to compensate the inaccuracy of the predefined hyperemic boundary condition parameter. A result thereof the personalized hyperemic boundary condition model is provided, which provides hyperemic boundary condition parameters, which are suitable to condition the parametric model, such that an accurate blood flow simulation of the human subject is ensured. Such a simulation in particular simulates the blood flow in the exemplary explained coronary tree 34 with increased blood flow resistance. Thus, the at least one morphological feature as a personalized feature of the human subject may provide a good basis for adjusting and/or adapting a hyperemic boundary condition for the parametric model, in order to allow an accurate simulation of the blood flow through the coronary tree 34, which in turn provides an enhanced fractional flow reserve determination result.

According to a preferred embodiment, at least one personalized feature represents an anatomical feature of the coronary tree 34 and at least one further personalized feature represents at least one morphological feature of the coronary tree 34. In the same manner, even a further type of a personalized feature may be taken into account. For instance, at least one personalized feature may represent at least one spectral feature of the coronary tree 34.

The differences in the Hounsfield unit (HU) value in the image shown in FIG. 3 illustrates, that the right coronary artery 36 as such and its surrounding tissue 40 may relate to different Hounsfield units. Thus, a spectral feature of the coronary tree 34, and in particular of the right coronary artery 36 as such and/or its surrounding tissue 40, may indicate a property of the coronary tree 34. In particular, the spectral feature may represent a concentration of plaque material in the coronary tree 34. Thus, if surrounding tissue 40 may be subject to plaque deposits, this may have a respective impact on the coronary tree 34, in particular to the flow resistance of the coronary tree 34. However, there may be differences in the plaque material as such. For instance, calcium plaque deposit and fatty plaque deposit may result in different impacts on the blood flow resistance. Thus, different plaque materials may have different effect on the coronary tree 34. Further, different plaque materials result in different spectral image results. For instance, calcium plaque may relate to a different Hounsfield unit than fatty plaque. Consequently, a spectral feature extracted from the volumetric image data may also form a personalized feature, and in turn may form a basis for adapting the hyperemic boundary condition model to account for human subject's specific coronary tree properties. In other words, at least one personal feature represented by at least one spectral feature could provide a good basis to adapt the hyperemic boundary condition model, resulting in the personalized hyperemic boundary condition model, which in turn allows to condition the parametric model, such that an enhanced fractional flow reserve can be calculated via a respective blood flow simulation.

Moreover, a combination of different types of personalized features, for instance of the group of anatomical features, morphological features and/or spectral features, may provide an even more synergistic indication for a property of the coronary tree 34 of the human subject under examination. In this context, reference is made to the introduction, where it has been explained, that a capillary's resistance may be auto-regulated to account for the presence of stenosis of a parent coronary. Even though non-imaged vasculature of the human subject under examination may not be extracted from the volumetric image data, the at least one personalized feature, and in particular a combination of personalized features, may provide the basis for taking such non-imaged vasculature into account and in turn may provide a good basis for adapting the hyperemic boundary condition model resulting in the personalized hyperemic boundary condition model.

There are several optional relations between a microvasculature resistance and a personalized feature, in particular an anatomical feature, a physiological feature and/or a spectral feature. One option to model the blood flow resistance as a function of a coronary outlet cross-sectional area is used in the experimental results described in the letter "Learning patient-specific lumped models for interactive coronary blood flow simulations", by Nickisch et al., in Medical Imaging Computing and Computer-Assisted Intervention, 2015, pages 433-441, Springer International Publishing, to describe the relation between blood flows in a coronary tree 34 and/or in its coronary vessels with respect to their respective diameter by the following model equation:

$$R_i = R_0 \cdot \frac{r_{in}^{1/3} \cdot \rho_{blood} \cdot r_{out,i}^{-7/3}}{\pi} \left[\frac{g}{cm^4 \cdot s}\right] \qquad \text{Eq. 1}$$

In the model equation (Eq. 1), $R_i$ is the outlet blood flow resistance of a coronary vessel, wherein $R_0$ is the base overall resistance, in particular accounting (micro-) vasculature blood flow resistance impacts, and $\rho_{blood}$ is the (predefined) blood density. The base resistance $R_0$ scales directly with the inlet radius $r_{in}$ of the respective coronary vessel and with the outlet radius $r_{out}$ of the coronary vessel to get the outlet blood flow resistance $R_i$. Preferably, the outlet blood flow resistance is assigned to an outlet of the respective coronary vessel. An effective radius of the coronary vessel can be calculated from its cross-sectional area (CSA) with the following equation:

$$r = \sqrt{\frac{CSA}{\pi}} \qquad \text{Eq. 2}$$

The base resistance $R_o$, the inlet radius $r_{in}$ and the outlet radius $r_{out}$ may be provided as predefined hyperemic boundary condition parameters provided by the hyperemic boundary condition model. Thus, each of said parameters may relate to empirical parameters. For instance, the base resistance $R_0$ can be found by a machine-learning approach, where a set of training data with intensively measured fractional flow reserve values ($FFR_{GT}$) and predicted fractional flow reserve values ($FFR_{CT}$), which are based on tomography image data, is used to find the base resistance $R_0$ that maximizes the following classifier performance:

$$\tilde{R_0} = \underset{R_0}{\arg\max}\, AUC(FFR_{CT}(R_0, r_{in}, r_{out,i}), FFR_{GT}) \qquad \text{Eq. 3}$$

However, as explained above, the predefined hyperemic boundary condition parameter and in turn the hyperemic boundary condition parameter model may not specify individual properties of the human subject under examination. Therefore, according to an exemplary embodiment, a further personalized hyperemic boundary condition parameter in form of a personalization function f(patient-features) may be used in order to personalize the set of hyperemic boundary condition parameters, which is provided by the personalized hyperemic boundary condition parameter model. Thus, in order to determine the output resistance $R_i$ of a coronary vessel, the following equation may be used:

$$R_i = R_0 \cdot f(\text{patient} - \text{features}) \cdot \frac{r_{in}^{1/3} \cdot \rho_{blood} \cdot r_{out,i}^{-7/3}}{\pi} \left[\frac{g}{cm^4 \cdot s}\right] \qquad \text{Eq. 4}$$

where f(patient-features): $R^n \rightarrow R$ is the personalization function that relates the at least one personalized feature described above to the human subject's (personalized) hyperemic boundary condition parameters. For example, in case of considering the coronary tree inlet of the coronary tree 34 as a personalized feature, in order to allow an enhanced blood flow simulation of the coronary tree 34 of the human subject, the personalization function f(patient-features) may be taken from:

$$f(\text{patient} - \text{features}) = \left(\min\left(2, \frac{A_0}{r_{in}^2}\right)\right)^q \qquad \text{Eq. 5}$$

In this equation (Eq. 5), $A_o$ may relate to a normalized factor and q is an indicator to control whether the hyperemic boundary conditions are personalized according to the inlet radius (q=1) or not (q=0).

Moreover, the parameters $R_o$, $A_o$ can be found by a machine-learning algorithm, where a set of training data within invasively measured fractional flow reserve values ($FFR_{GT}$) is used to find the parameters $R_o$, $A_o$ that maximizes the FFR-CT based classifier function:

$$\widetilde{R_0, A_0} = \underset{R_0, A_0}{\arg\max}\, AUC(FFR_{CT}(R_0, A_0, r_{in}, r_{out,i}), FFR_{GT}) \qquad \text{Eq. 6}$$

The function internal weighting parameters can be found using an optimization technique.

In the case of considering plaque in the coronary tree 34, the respective at least one morphological feature as the at least one personalized feature may describe plaque deposits and may be indicative for the blood flow in the coronary tree 34 of the human subject under examination. The respective at least one personalized features can represent total plaque volume, a calcified plaque volume, a non-calcified plaque volume, a number of calcified spots in the coronary tree 34, a length, in particular total length, of a plaque deposit and/or others. Then, the at least one personalized hyperemic boundary condition parameter may form a relationship between the plaque and a respective scaling of the blood flow resistance.

In the case of considering the plaque morphology, the (patient-features) $\in R^n$ is a feature vector describing plaque morphology features. Then, the personalization function f(patient-features): $R^n \to R$ is forming the relationship between the plaque morphology features and the scaling of the output blood flow resistance $R_i$ may be described by $$R_0, f\_internal = \underset{R_0, f_{internal}}{\arg\max} \quad \text{Eq. 7}$$

$$AUC(FFR_{CT}(R_0, f_{internal}, \text{patient-features}, r_{out,i}), FFR_{GT})$$

The function internal weighting parameters can be found using an optimization technique.

In case of considering at least one spectral feature, which may relate to plaque in the coronary tree 34, in particular to a concentration of plaque material in the coronary tree 34, the (patient-features)$\in R^n$ is a feature vector, which may describe plaque spectral features. These features can be derived from spectral CT imaging data of the human subject, and may include the effective atomic number content of the plaque, plaque appearance at different energy levels, among others. Then, the personalization function f(patient-features):$R^n \to R$ is forming the relationship between the plaque spectral features and the scaling of the output blood flow resistance $R_i$. The function internal weighting parameters can be found using an optimization technique.

In view of the explanations provided above and according to one preferred embodiment, the processing unit 30 may therefore be configured to determine at least one personalized hyperemic boundary condition parameter based on the at least one personalized feature, wherein the processing unit 30 is configured to adapt the hyperemic boundary condition model, such that the resulting personalized hyperemic boundary condition model comprises the at least one predefined hyperemic boundary condition parameter and the at least one personalized hyperemic boundary condition parameter. However, instead of comprising a (further) personalized hyperemic boundary condition parameter, the at least one personalized feature may be used to adjust and/or adapt at least one of the predefined hyperemic boundary condition parameters resulting in a (now) personalized hyperemic boundary condition parameter. Thus, the processing unit 30 may also be configured to determine the personalized hyperemic boundary condition model by adapting and/or adjusting the at least predefined hyperemic boundary condition parameter based on the at least one personalized feature.

Figure 4:
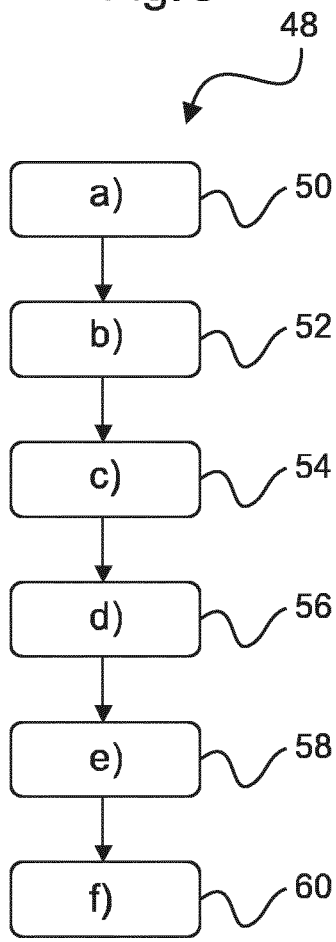
FIG. 4 schematically illustrates a flow chart of an embodiment of the method.

FIG. 4 schematically illustrates an example of a flowchart 48 of a method according to the invention for determining a fractional flow reserve. The method comprises the following:

In a first step 50, also referred to as step a), volumetric image data representing a coronary tree 34 of a human subject is obtained.

In a second step 52, also referred to as step b), a parametric model for simulating a blood flow in a coronary tree 34 is provided.

In a third step 54, also referred to as step c), a hyperemic boundary condition model representing at least one predefined hyperemic boundary condition parameter for the parametric model is provided.

In a fourth step 56, also referred to as step d), at least one personalized feature is extracted from the volumetric image data.

According to a fifth step 58, also referred to as step e), the hyperemic boundary condition model is adapted based on the at least one personalized feature resulting in a personalized hyperemic boundary condition model.

In a sixth step 60, also referred to as step f), a fractional flow reserve of a coronary vessel of the coronary tree 34 of the human subject is determined with the parametric model and the personalized hyperemic boundary condition model.

It is understood that, without repeating here all the explanations, examples, features and/or advantages provided in reference to the apparatus 26, the method of the invention is intended to be configured to carry out the method steps 50 to 60 for which the apparatus 26 is configured to. Thus, all the above examples, explanations, features and/or advantages, although provided previously with reference to the apparatus 26, are also intended to be provided in an analogous manner for the method, in particular for the following exemplary embodiments of the method.

According to an exemplary embodiment of the method, the volumetric image data represents the coronary tree of the human subject in a rest state.

According to a further exemplary embodiment of the method, the processing unit is configured to determine the fractional flow reserve of the coronary vessel of the coronary tree of the human subject in a hyperemic state.

According to a further exemplary embodiment of the method, the volumetric image data is formed by cardiac computed tomography angiography image date.

According to an exemplary embodiment of the method, the method comprises a sub-step, wherein at least one personalized hyperemic boundary condition parameter is determined based on the at least one personalized feature. The method may comprise a further sub-step, wherein the hyperemic boundary condition model is adapted, such that the resulting personalized hyperemic boundary condition model comprises the at least one predefined hyperemic boundary condition parameter and the at least one personalized hyperemic boundary condition parameter.

According to an exemplary embodiment of the method, the personalized hyperemic boundary condition model is determined by adapting at least one predefined hyperemic boundary condition parameter based on the at least one personalized feature.

According to a further exemplary embodiment of the method, at least one personalized feature represents at least one anatomical feature of the coronary tree.

According to a further exemplary embodiment of the method, at least one anatomical feature represents a cross-section of a segment of the coronary tree.

According to a further exemplary embodiment of the method, at least one personalized feature represents at least one morphological feature of the coronary tree.

According to a further exemplary embodiment of the method, at least one morphological feature represents plaque in the coronary tree.

According to a further exemplary embodiment of the method, at least one personalized feature represents at least one spectral feature of the coronary tree.

According to a further exemplary embodiment of the method, at least one spectral feature represents a concentration of plaque material in the coronary tree.

According to a further example of the present invention, a computer program element is provided, which, when being executed by a processing unit is adapted to carry out the method described above.

According to further example of the present invention, a computer readable medium having stored thereon a program element is provided, which, when being executed by a processing unit is adapted to carry out the method described above.

It has to be noted that embodiments of the invention are described with reference to different subject matters. In particular, some embodiments are described with reference to a method whereas other embodiments are described with reference to the apparatus. However, a person skilled in the art will gather from the above that, unless otherwise notified, in addition to any combination of features belonging to one subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single parameter, feature or other element may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for determining a fractional flow reserve, comprising:
    an input,
    processor circuitry, and
    a storage;
    wherein the input is configured to obtain volumetric image data representing a coronary tree of a human subject, wherein the volumetric image data represents at least a section of the coronary tree of the human subject;
    wherein the storage is configured to provide a parametric model for simulating a blood flow in a coronary tree;
    wherein the storage is configured to provide a hyperemic boundary condition model representing at least one predefined hyperemic boundary condition parameter for the parametric model;
    wherein the processor circuitry is configured to extract at least one personalized feature from the volumetric image data, wherein the at least one personalized feature represents at least one morphological feature of the coronary tree, and wherein the at least one morphological feature of the coronary tree relates to and/or represents a feature of a tissue forming a surrounding surface of a coronary vessel of the coronary tree;
    wherein the processor circuitry is configured to adapt the hyperemic boundary condition model based on the at least one personalized feature resulting in a personalized hyperemic boundary condition model representing at least one personalized hyperemic boundary condition parameter for the parametric model; and
    wherein the processor circuitry is configured to determine a fractional flow reserve of the coronary vessel of the coronary tree of the human subject with the parametric model and the personalized hyperemic boundary condition model.

2. The apparatus according to claim 1, wherein the processor circuitry is configured to determine the fractional flow reserve of the coronary vessel of the coronary tree of the human subject in a hyperemic state.

3. The apparatus according to claim 1, wherein the volumetric image data is formed by cardiac computed tomography angiography image data.

4. The apparatus according to claim 1, wherein the processor circuitry is configured to determine the at least one personalized hyperemic boundary condition parameter based on the at least one personalized feature, and wherein the processor circuitry is configured to adapt the hyperemic boundary condition model, such that the resulting personalized hyperemic boundary condition model comprises the at least one predefined hyperemic boundary condition parameter and the at least one personalized hyperemic boundary condition parameter.

5. The apparatus according to claim 1, wherein the at least one personalized feature represents at least one anatomical feature of the coronary tree.

6. The apparatus according to claim 5, wherein the at least one anatomical feature represents a cross-section of a segment of the coronary tree.

7. The apparatus according to claim 1, wherein the at least one morphological feature represents plaque in the coronary tree.

8. The apparatus according to claim 1, wherein the at least one personalized feature represents at least one spectral feature of the coronary tree.

9. The apparatus according to claim 1, wherein the at least one spectral feature represents a concentration of plaque material in the coronary tree.

10. A method for determining a fractional flow reserve, comprising:
    obtaining volumetric image data representing a coronary tree of a human subject, wherein the volumetric image data represents at least a section of the coronary tree of the human subject;
    providing a parametric model for simulating a blood flow in a coronary tree;
    providing a hyperemic boundary condition model representing at least one predefined hyperemic boundary condition parameter for the parametric model;
    extracting at least one personalized feature from the volumetric image data, wherein the at least one personalized feature represents at least one morphological feature of the coronary tree, and wherein the at least one morphological feature of the coronary tree relates to and/or represents a feature of a tissue forming a surrounding surface of a coronary vessel of the coronary tree;

adapting the hyperemic boundary condition model based on the at least one personalized feature resulting in a personalized hyperemic boundary condition model representing at least one personalized hyperemic boundary condition parameter for the parametric model; and determining a fractional flow reserve of a coronary vessel of the coronary tree of the human subject with the parametric model and the personalized hyperemic boundary condition model.

11. A non-transitory computer-readable medium having one or more executable instructions stored thereon, which, when executed by a processor, cause the processor to perform a method for determining a fractional flow reserve, comprising:

obtaining volumetric image data representing a coronary tree of a human subject, wherein the volumetric image data represents at least a section of the coronary tree of the human subject;

providing a parametric model for simulating a blood flow in a coronary tree;

providing a hyperemic boundary condition model representing at least one predefined hyperemic boundary condition parameter for the parametric model;

extracting at least one personalized feature from the volumetric image data, wherein the at least one personalized feature represents at least one morphological feature of the coronary tree, and wherein the at least one morphological feature of the coronary tree relates to and/or represents a feature of a tissue forming a surrounding surface of a coronary vessel of the coronary tree;

adapting the hyperemic boundary condition model based on the at least one personalized feature resulting in a personalized hyperemic boundary condition model representing at least one personalized hyperemic boundary condition parameter for the parametric model; and determining a fractional flow reserve of a coronary vessel of the coronary tree of the human subject with the parametric model and the personalized hyperemic boundary condition model.

* * * * *